(12) United States Patent
Ruiz

(10) Patent No.: US 8,206,991 B2
(45) Date of Patent: Jun. 26, 2012

(54) PARTICLE SENSOR

(75) Inventor: Victoriano Ruiz, Roscommon, MI (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 13/234,497

(22) Filed: Sep. 16, 2011

(65) Prior Publication Data

US 2012/0009688 A1   Jan. 12, 2012

Related U.S. Application Data

(62) Division of application No. 11/882,217, filed on Jul. 31, 2007.

(51) Int. Cl.
*G01N 25/20* (2006.01)
*G01N 25/00* (2006.01)

(52) U.S. Cl. ........................... 436/147; 436/145
(58) Field of Classification Search ............... 436/147; 422/82.12, 68.1, 50
See application file for complete search history.

(56) References Cited

U.S. PATENT DOCUMENTS

| | | | |
|---|---|---|---|
| 4,307,061 A | * | 12/1981 | Sarholz ............................ 422/94 |
| 4,500,412 A | | 2/1985 | Takahashi et al. |
| 4,656,832 A | | 4/1987 | Yukihisa et al. |
| 5,352,353 A | | 10/1994 | Schonauer et al. |
| 6,306,315 B1 | | 10/2001 | Ogata et al. |
| 6,432,168 B2 | | 8/2002 | Schonauer |
| 6,634,210 B1 | | 10/2003 | Bosch et al. |
| 6,971,258 B2 | | 12/2005 | Rhodes et al. |
| 7,017,338 B2 | | 3/2006 | van Nieuwstadt |
| 7,056,453 B2 | | 6/2006 | Ogata et al. |
| 7,138,901 B2 | | 11/2006 | Seshadri et al. |
| 2001/0035044 A1 | | 11/2001 | Larsson et al. |
| 2001/0051108 A1 | | 12/2001 | Schonauer |
| 2005/0091970 A1 | | 5/2005 | Nieuwstadt |
| 2005/0225422 A1 | | 10/2005 | Seshadri et al. |
| 2007/0089478 A1 | | 4/2007 | Wirth et al. |

FOREIGN PATENT DOCUMENTS

GB     2029028     3/1980

* cited by examiner

*Primary Examiner* — Christine T Mui
(74) *Attorney, Agent, or Firm* — Finnegan, Henderson, Farabow, Garrett & Dunner LLP

(57) ABSTRACT

A particle sensor is provided having a first temperature sensing device having a sensing surface exposed to particles contained within a fluid. The sensing surface is at least partially coated with a catalyst for promoting an exothermic reaction with at least a portion of the particles. The particle sensor also has a second temperature sensing device positioned at a location substantially thermally isolated from thermal energy generated by the exothermic reaction.

17 Claims, 2 Drawing Sheets

PARTICLE SENSOR

CROSS-REFERENCE TO RELATED APPLICATION

This patent application is a Divisional of U.S. patent application Ser. No. 11/882,217, filed Jul. 31, 2007. Which is hereby fully incorporated by reference.

TECHNICAL FIELD

The present disclosure is directed to a particle sensor and, more particularly, to a particle sensor utilizing temperature sensing devices.

BACKGROUND

Engines, including diesel engines, gasoline engines, natural gas engines, and other engines known in the art, may exhaust a complex mixture of air pollutants. The air pollutants may include both gaseous and solid material, such as, for example, particulate matter. Particulate matter may include ash and unburned carbon particles and may sometimes be referred to as soot.

Due to increased environmental concerns, among other things, exhaust emission standards may have become more stringent. The amount of particulate matter and gaseous pollutants emitted from an engine may be regulated depending on the type, size, and/or class of engine. In order to meet these emissions standards, engine manufacturers have pursued improvements in several different engine technologies, such as fuel injection, engine management, and air induction, to name a few. In addition, engine manufacturers have developed devices for treatment of engine exhaust after it leaves the engine.

Engine manufacturers have employed exhaust treatment devices called particulate traps to remove the particulate matter from the exhaust flow of an engine. A particulate trap may include a filter designed to trap particulate matter. The use of the particulate trap for extended periods of time, however, may enable particulate matter to accumulate on the filter, thereby causing damage to the filter and/or a decline in engine performance. Systems have been developed to measure, or estimate, an amount of particulate matter that has accumulated on the filter.

For example, one such system for soot detection is described in U.S. Patent Publication No. US2001/0051108 (the publication) by Schonauer. The publication describes an apparatus for detecting soot. The apparatus includes a porous ceramic element, a heater, a first temperature probe, and a second temperature probe. The heater applies a constant level of heat to the porous ceramic element that is equivalent to the minimum ignition temperature of soot. As exhaust gas containing soot passes through the pores of the ceramic element, the exhaust gas is heated to the soot ignition temperature combusting the soot and further increasing the temperature of the exhaust gas. Such a temperature increase is measured by the first temperature probe. At the same time, a portion of the exhaust gas is directed to a chamber through a filter, which filters most of the soot contained within the exhaust gas. Because the exhaust gas in the chamber contains such a small amount of soot, the temperature of exhaust gas in the chamber provides a baseline temperature for comparison with the temperature increase measured by the first temperature probe. Such a baseline temperature is measured by the second temperature probe. The difference between the two temperatures is directly related to the amount of soot contained within the exhaust gas.

Although the apparatus described in the publication may detect the amount of soot contained within the exhaust gas, the design may be prone to inaccuracies. In particular, because the exhaust gas is heated to the ignition temperature of soot before reaching both temperature probes, any soot that is allowed to reach the second temperature probe may compromise soot level measurements. To isolate the second temperature probe from soot contained within the exhaust gas, a filtering element and an isolation chamber must be built within the sensor housing. Inherent manufacturing inconsistencies may limit the filtering capability of any filtering element, and unknown levels of soot may infiltrate the isolation chamber. These manufacturing inconsistencies may limit the accuracy of any soot level measurement by distorting the baseline temperature due to undesired soot combustion.

In addition, the apparatus described in the publication may be limited to only the detection of soot because it relies on heating the exhaust gas to the ignition temperature of soot. However, it may be desired to detect the level of other types of pollutants contained within the exhaust gas. Preheating the exhaust gas to determine the level of such pollutants may not be preferred because the pollutants may have ignition temperatures that may be difficult to attain or may damage other equipment in the exhaust system.

The disclosed apparatus is directed to overcoming one or more of the problems set forth above.

SUMMARY OF THE INVENTION

In one aspect, the disclosure is directed toward a particle sensor. The particle sensor includes a first temperature sensing device having a sensing surface exposed to particles contained within a fluid. The sensing surface is at least partially coated with a catalyst for promoting an exothermic reaction with at least a portion of the particles. The particle sensor also includes a second temperature sensing device positioned at a location substantially thermally isolated from thermal energy generated by the exothermic reaction.

Consistent with a further aspect of the disclosure, a method is provided for sensing particles in a fluid. The method includes promoting an exothermic chemical reaction between a catalyst and at least a portion of the particles contained within the fluid. The method also includes sensing a parameter indicative of a temperature of the exothermic chemical reaction. The method further includes sensing a parameter indicative of a temperature of the fluid. In addition, the method includes determining a temperature difference between the sensed temperature of the exothermic chemical reaction and the sensed temperature of the fluid.

DETAILED DESCRIPTION

Figure 1:
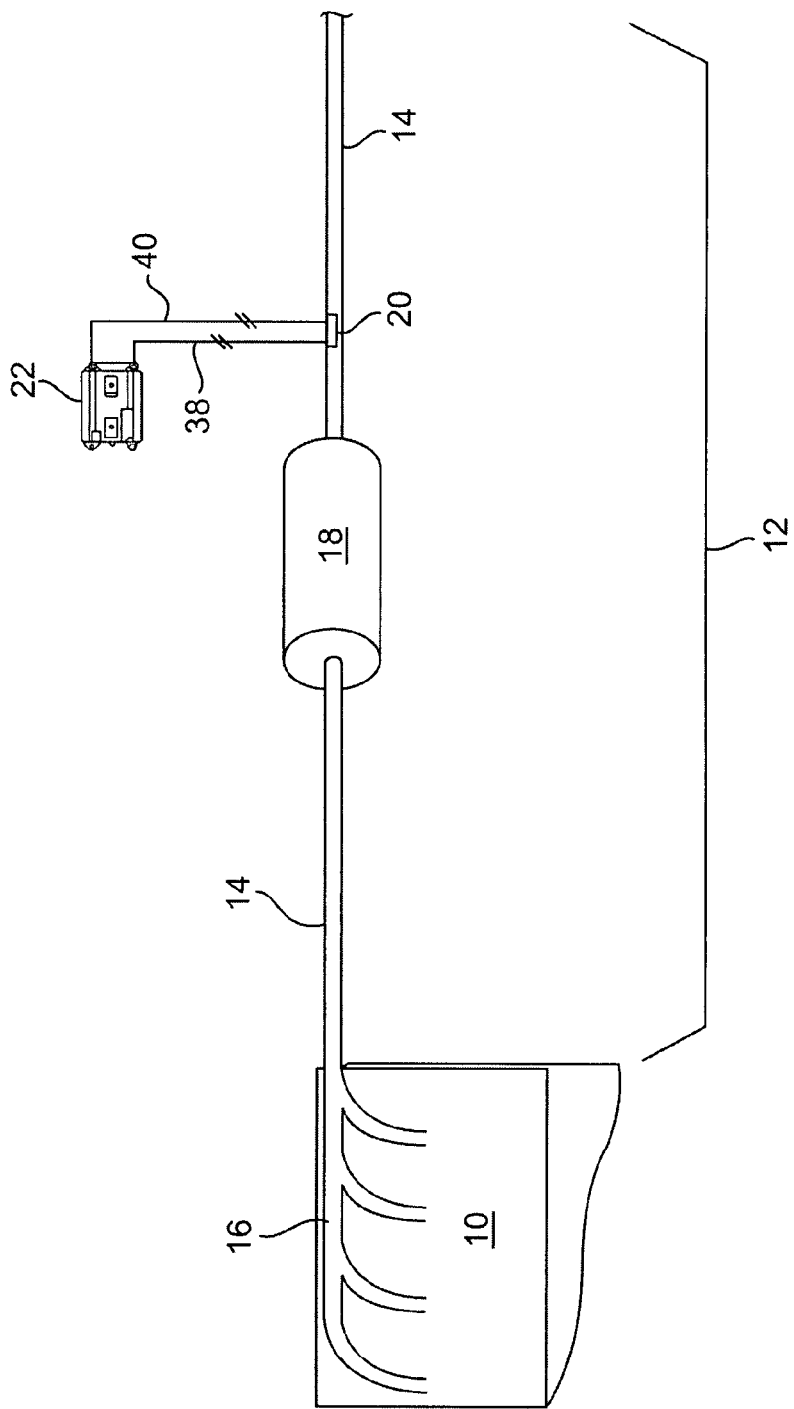
FIG. 1 is a diagrammatic illustration of an exemplary disclosed power source and associated exhaust system.

FIG. 1 illustrates an exemplary power source 10 including an internal combustion engine having multiple subsystems that cooperate to produce mechanical or electrical power output. For the purposes of this disclosure, power source 10 is depicted and described as a four-stroke diesel engine. One skilled in the art will recognize, however, that power source 10 may be any other type of internal combustion engine such as, for example, a gasoline or a gaseous fuel-powered engine. One subsystem included within power source 10 may be an exhaust system 12. Other subsystems included within power source 16 may be, for example, a fuel system, an air induction system, a lubrication system, a cooling system, or any other appropriate system (not shown).

Exhaust system 12 may remove or reduce the amount of pollutants in the exhaust produced by power source 10 and release the treated exhaust into the atmosphere. Exhaust system 12 may include an exhaust passage 14 which may be in fluid communication with an exhaust manifold 16 of power source 10. Exhaust system 12 may also include an exhaust treatment device 18 fluidly connected to exhaust passage 14, a particle sensor 20, and a controller 22. Exhaust treatment device 18 may be, for example, a catalytic device, a particulate trap, an attenuation device, or any device capable of removing pollutants from exhaust gas flowing through exhaust passage 14. Although exhaust system 12 is illustrated including only one exhaust treatment device 18, it is contemplated that exhaust treatment system 12 may include multiple exhaust treatment devices 18, if desired.

Figure 2:
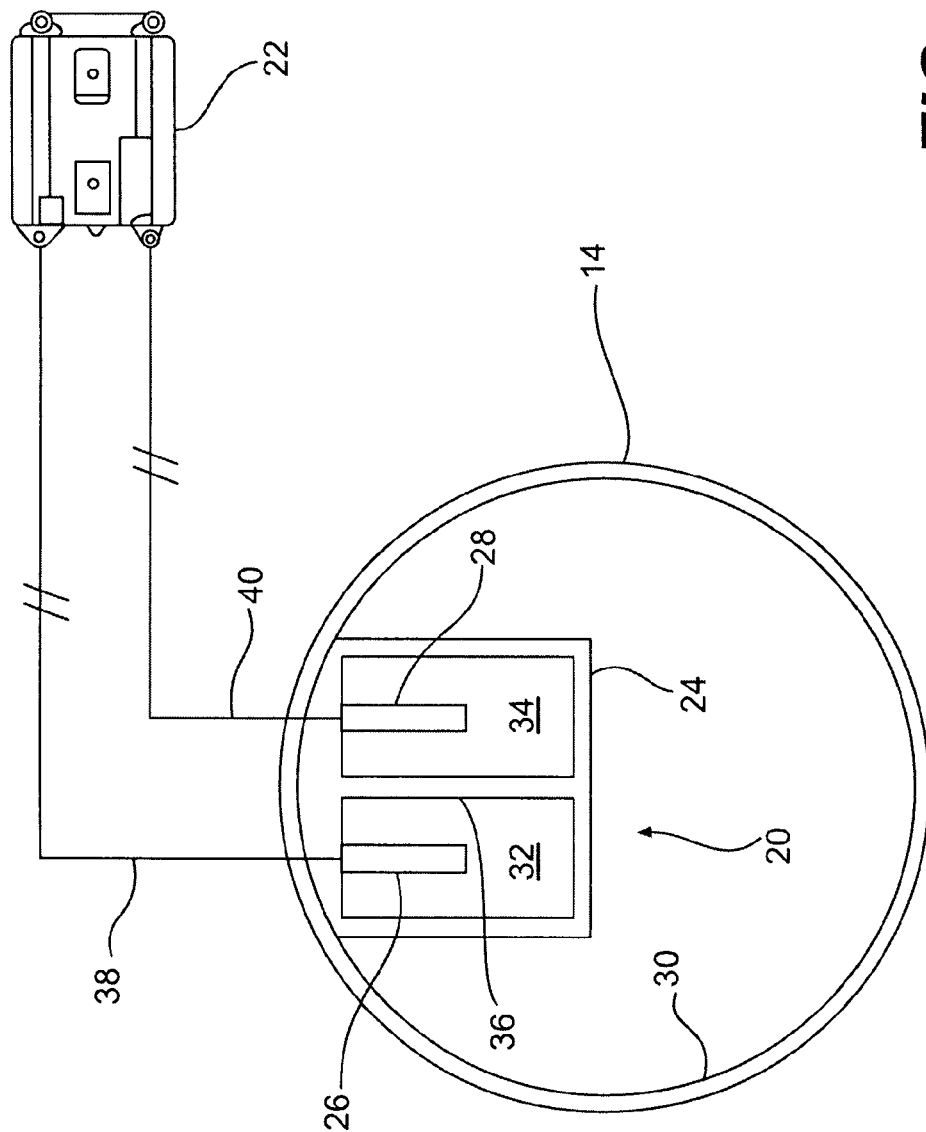
FIG. 2 is a schematic diagram of a particle sensor for use with the exhaust system of FIG. 1.

As illustrated in FIG. 2, particle sensor 20 may include a housing 24 enclosing a first temperature probe 26 and a second temperature probe 28. Housing 24 may be secured to an interior surface 30 of exhaust passage 14 using any method or device such as, for example, welds, mechanical fasteners, or adhesives. It is contemplated that housing 24 may be any shape capable of permitting exhaust gas to flow freely. However, it may be desired to select a housing shape that produces minimal drag to reduce any backpressure that may adversely affect the performance of exhaust system 12. Housing 24 may define passages 32 and 34 through which exhaust gas may flow. A wall member 36 may divide and reduce heat transfer between passages 32 and 34. In addition, wall member 36 may be manufactured from any type of rigid material having strong insulating properties such as, for example, heat resistant ceramics or foams.

First and second temperature probes 26 and 28 may be situated within passages 32 and 34 so that they are exposed to the exhaust gas flowing through housing 24. In addition, first and second temperature probes may be for example, a thermocouple, a thermistor, or any other type of temperature sensing device capable of sending a signal indicative of an exhaust gas temperature to controller 22. First and second temperature probes may communicate with controller 22 via communication lines 38 and 40, respectively. It is contemplated that, for increased accuracy, first and second temperature probes 32 and 34 may have similar sensing properties. For example, in embodiments utilizing thermistors, first and second temperature probes 26 and 28 may have substantially similar resistance characteristics. Also, in embodiments utilizing thermocouples, first and second temperature probes 26 and 28 may have substantially similar voltage generating characteristics.

An entire surface of first temperature probe 26 exposed to the exhaust gas may be coated with a catalyst. The catalyst may be any material capable exothermically reacting with a particular type of particle contained within the exhaust gas. The particle may be, for example, soot, sulfur, or any other type of emissions particle that may be regulated. In addition, the catalyst may be selected so that it may exothermically react only with the type of particle for which detection is desired. When a particular type of particle contained within exhaust gas encounters temperature probe 26, the resulting exothermic reaction with the catalyst may increase the temperature of exhaust gas flowing through passage 32 by a magnitude directly related to the amount of the particle contained within the exhaust gas.

Controller 22 may include one or more microprocessors, a memory, a data storage device, a communication hub, and/or other components known in the art and may be associated with exhaust system 12. Controller 22 may receive signals from first and second temperature probes 26 and 28 and analyze the data to determine a difference between the temperature of exhaust gas flowing through passage 32 and the temperature of exhaust gas flowing through passage 34. Controller 22 may compare the determined difference to algorithms, equations, tables, or charts stored in or accessible by controller 22 to determine the amount of the sensed particle contained within the exhaust gas. Based on the quantity of the particle, controller 22 may establish an output to influence the operation of other devices of exhaust system 12.

Industrial Applicability

The disclosed particle sensor may accurately detect the quantity of a particular type of particle such as, for example, soot that may be contained within an exhaust gas. In particular, the disclosed particle sensor may provoke an exothermal chemical reaction between the soot and a catalyst. The resulting temperature increase may be directly related to the amount of soot within the exhaust gas. The operation of particle sensor 20 will now be explained.

Exhaust gas may flow through exhaust passageway 14 and enter sensor 20 via passages 32 and 34. In passage 34, first temperature probe 26 may be exposed to the exhaust gas flowing through passage 32. The first temperature probe 26 may be coated with a catalyst that may exothermally react only with soot. As the exhaust gas encounters first temperature probe 26, the catalyst may exothermically react with the soot increasing the temperature of the exhaust gas surrounding the reaction. First temperature probe 26 may send a temperature signal to controller 22 indicative of the increased exhaust gas temperature.

In passage 34, second temperature probe 28 may be exposed to exhaust gas flowing through passage 34. Unlike first temperature probe 26, an exposed surface of second temperature probe 28 may be left uncoated or coated with a chemically neutral material so that neither the exhaust gas nor particles within the exhaust gas may exothermically react with the exposed surface of second temperature probe 28. In addition, wall member 36 may insulate second temperature probe 28 and the exhaust gas flowing through passage 34 from the heat generated by the exothermic reaction occurring in passage 32. It is contemplated that wall member 36 may be omitted if second temperature probe 28 is positioned far enough from first temperature probe 26 to be unaffected by the exothermic reaction. This may allow second temperature 28 to sense a baseline temperature of the exhaust gas. Second temperature probe 28 may send a temperature signal to controller 22 indicative of the baseline exhaust gas temperature.

Upon receiving the temperature signals from first and second temperature probes 26 and 28, controller 22 may calculate the difference between the two sensed temperatures, which may be directly related to the amount of soot contained within the exhaust gas. Controller 22 may compare the calculated temperature difference to tables, graphs, and/or equations stored in its memory or accessible to controller 22 to determine the amount of soot contained within the exhaust gas. Once the amount of soot is determined, controller 22 may perform any number of predetermined actions. For example, controller 22 may actuate a regenerating device to regenerate a particulate trap filter or actuate a warning alarm if the level of soot in the exhaust gas exceeds a predetermined threshold.

It should be understood that particle sensor 20 may be located anywhere within exhaust passageway 14 depending on the desired use of particle sensor 20.

Because the disclosed sensor does not preheat the exhaust gas before exposing the temperature probes to the exhaust gas, the disclosed sensor may generate more accurate readings. In particular, the disclosed sensor may not need to filter the soot before exposing the second temperature probe to the exhaust gas, and special devices such as filters and isolation chambers may not be necessary to generate an accurate baseline temperature reading. Without elements that require such tight manufacturing tolerances, inherent manufacturing inconsistencies may have less of an impact on the sensor's accuracy.

In addition, because the sensor relies on exothermic chemical reactions the sensor may not be limited to the detection of only soot. In particular, because the catalyst may generate the temperature increase, the types of particles which may be detected by the sensor may only be limited by the variety of catalysts known in the art.

It will be apparent to those skilled in the art that various modifications and variations can be made in the disclosed apparatus without departing from the scope of the disclosure. Other embodiments will be apparent to those skilled in the art from consideration of the specification disclosed herein. It is intended that the specification and examples be considered as exemplary only, with a true scope being indicated by the following claims and their equivalents.

What is claimed is:

1. A method for sensing particles in a fluid, comprising:
    promoting an exothermic chemical reaction between a catalyst on a portion of a first temperature sensing device and at least a portion of the particles contained within the fluid;
    sensing a parameter indicative of a temperature of the exothermic chemical reaction with the first temperature sensing device;
    sensing a parameter indicative of a temperature of the fluid with a second temperature sensing device that is thermally isolated from the first temperature sensing device; and
    determining a temperature difference between the temperature of the exothermic chemical reaction sensed by the first temperature sensing device and the temperature of the fluid sensed by the second temperature sensing device, wherein the temperature difference is indicative of an amount of the portion of the particles contained within the fluid.

2. The method of claim 1, wherein the exothermic chemical reaction is between the catalyst and only one type of particle contained within the fluid.

3. The method of claim 2, wherein the one type of particle is soot.

4. The method of claim 2, wherein the parameter indicative of the temperature of the exothermic chemical reaction is sensed by the first temperature sensing device disposed at a first location, and the parameter indicative of the temperature of the fluid is sensed by the second temperature sensing device at a second location either upstream or downstream from the first location.

5. The method of claim 2, wherein the parameter indicative of temperature for both the exothermic chemical reaction and the fluid is electrical resistance.

6. The method of claim 2, wherein the parameter indicative of temperature for both the exothermic chemical reaction and the fluid is electrical voltage.

7. The method of claim 2, wherein the parameter indicative of the temperature of the exothermic chemical reaction is sensed by the first temperature sensing device disposed at a first location, and the parameter indicative of the temperature of the fluid is sensed by the second temperature sensing device at a second location thermally isolated from the first temperature sensing device by an insulating barrier.

8. The method of claim 1, wherein the first and second temperature sensing devices have substantially similar electrical characteristics.

9. The method of claim 8, wherein the first and second temperature sensing devices are thermistors.

10. The method of claim 8, wherein the first and second temperature sensing devices are thermocouples.

11. A method for sensing particles in a fluid, comprising:
    sensing, with a first temperature sensing device, a temperature of the fluid;
    sensing, with a second temperature sensing device that is thermally isolated from the first temperature sensing device, a temperature resulting from an exothermic reaction between the particles in the fluid and a catalyst on the second temperature sensing device; and
    determining a quantity of the particles contained in the fluid based on the temperature difference between the temperatures sensed by the first and second temperature sensing devices.

12. The method of claim 11, wherein the exothermic reaction is between the catalyst and only one type of particle contained in the fluid.

13. The method of claim 12, wherein the one type of particle is soot.

14. The method of claim 11, wherein the first and second temperature sensing devices have substantially similar electrical characteristics.

15. The method of claim 14, wherein the first and second temperature sensing devices are thermistors.

16. The method of claim 14, wherein the first and second temperature sensing devices are thermocouples.

17. The method of claim 11, wherein an insulating barrier is disposed between the first and second temperature sensing devices to thermally isolate the second temperature sensing device from the first temperature sensing device.

* * * * *